US00PP35545P2

(12) United States Plant Patent
Van Dijk

(10) Patent No.: US PP35,545 P2
(45) Date of Patent: Dec. 12, 2023

(54) ANTHURIUM PLANT NAMED 'AN2429660'

(50) Latin Name: ***Anthurium andraeanum* L.**
Varietal Denomination: AN2429660

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,193

(22) Filed: May 18, 2023

(51) Int. Cl.
*A01H 5/02* (2018.01)
*A01H 6/10* (2018.01)

(52) U.S. Cl.
USPC ..... Plt./365
CPC ..... *A01H 6/10* (2018.05)

(58) Field of Classification Search
USPC ..... Plt./365
CPC ..... A01H 5/02
See application file for complete search history.

*Primary Examiner* — Kent L Bell
(74) *Attorney, Agent, or Firm* — Jondle & Associates, P.C.

(57) ABSTRACT

A new *Anthurium* plant named 'AN2429660' particularly distinguished by having weakly blistered and medium glossy, green, cordate and durable spathes that retain the original color for a very long period of time, dark green, medium glossy, ovate-cordate, durable leaves, white spadices with green tips, early and rich flowering continuously throughout the year, and a plant height of 38.0 cm to 43.0 cm is disclosed.

3 Drawing Sheets

Genus and species: *Anthurium andraeanum* L.
Variety denomination: 'AN2429660'.

BACKGROUND OF THE NEW PLANT

The present invention comprises a new and distinct variety of *Anthurium*, botanically known as *Anthurium andraeanum* L., and hereinafter referred to by the variety name 'AN2429660'. The new *Anthurium* plant is a product of a planned breeding program conducted by the inventor in Bleiswijk, the Netherlands. The objective of this breeding program was to create a new plant with a height of 38.0 cm to 43.0 cm having weakly blistered and medium glossy, green, cordate and durable spathes.

The new variety originated from a cross-pollination made in November 2012 in Bleiswijk, the Netherlands. The female parent was a light yellow-green *Anthurium* pot plant designated '18374-04' (unpatented), and the male parent was a green *Anthurium* pot plant designated '21958-07' (unpatented).

A single plant was selected from the progeny of the stated cross in December 2014. Asexual reproduction of the new variety by tissue culture in 2019 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 19, 2021 (Application no. 2021/2973), by Applicant who obtained the subject matter disclosed directly from the inventor. 'AN2429660' has not been made publicly available or sold anywhere in the world prior to the effective filing date of this application with the exception of sales or disclosures made one year or less before the effective filing date of this claimed invention by Applicant who obtained 'AN2429660' directly from the inventor.

SUMMARY OF THE INVENTION

The following are the most outstanding and distinguishing characteristics of this new variety when grown under normal horticultural practices in Bleiswijk, the Netherlands:

1) Weakly blistered and medium glossy, green, cordate and durable spathes;
2) White spadices with green tips;
3) Dark green, medium glossy, ovate-cordate leaves;
4) Spathe: shape in cross section of middle zone is slightly concave; and
5) Spathe: position compared to leaves is slightly above.

DESCRIPTION OF THE PHOTOGRAPHS

This new *Anthurium* plant is illustrated by the accompanying photographs which show the overall plant habit including blooms, buds, and foliage of the plant; the colors shown are as true as can be reasonably obtained by conventional photographic procedures. The photographs are of a 44-week-old plant grown in a greenhouse in Bleiswijk, the Netherlands, in February 2023. Colors in the photographs may differ from the color values cited in the detailed botanical description, which accurately describe the actual colors of the new variety.

DESCRIPTION OF THE NEW VARIETY

Figure 1:
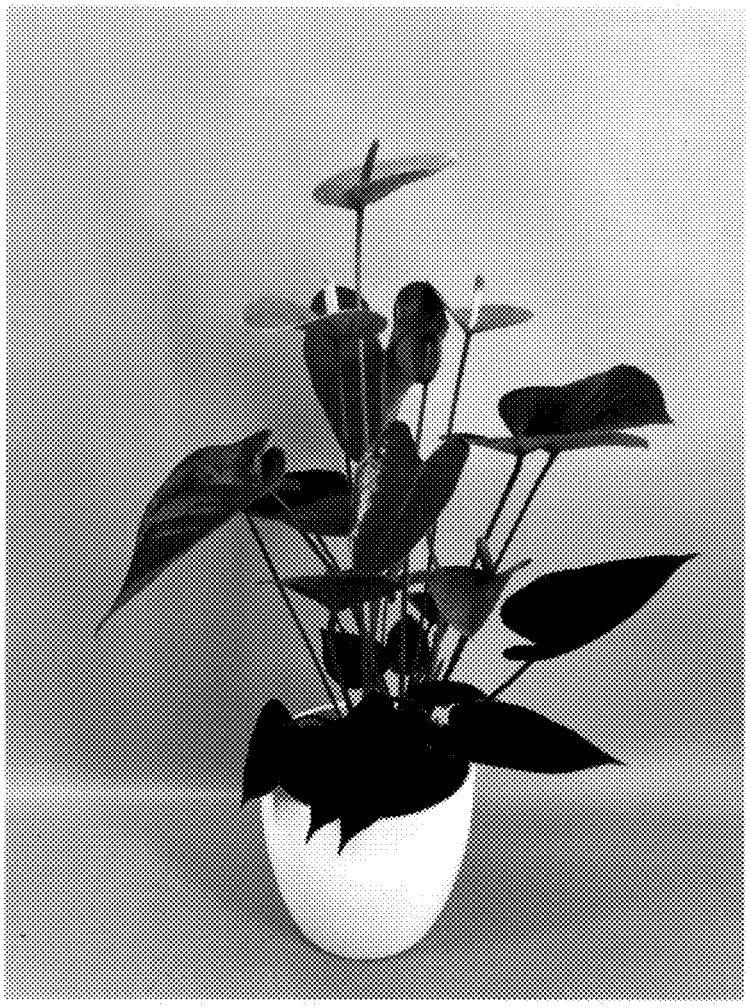
FIG. 1 shows the overall plant habit, including blooms, buds, and foliage.
Figure 2:
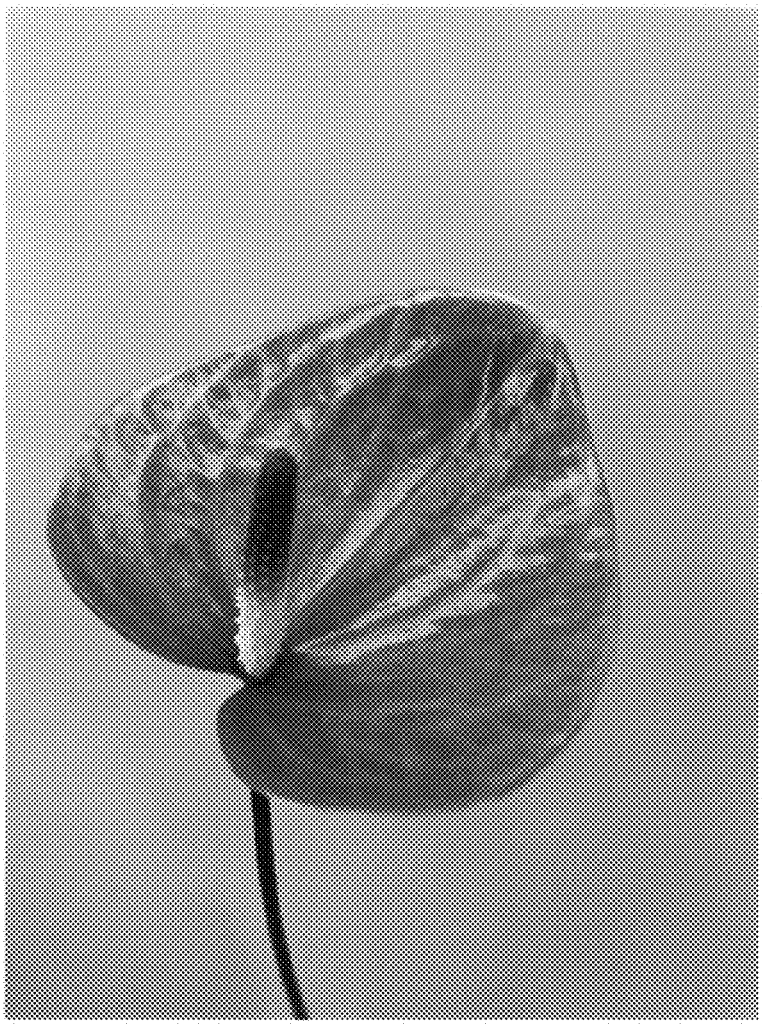
FIG. 2 shows a close-up of the mature spathe.
Figure 3:
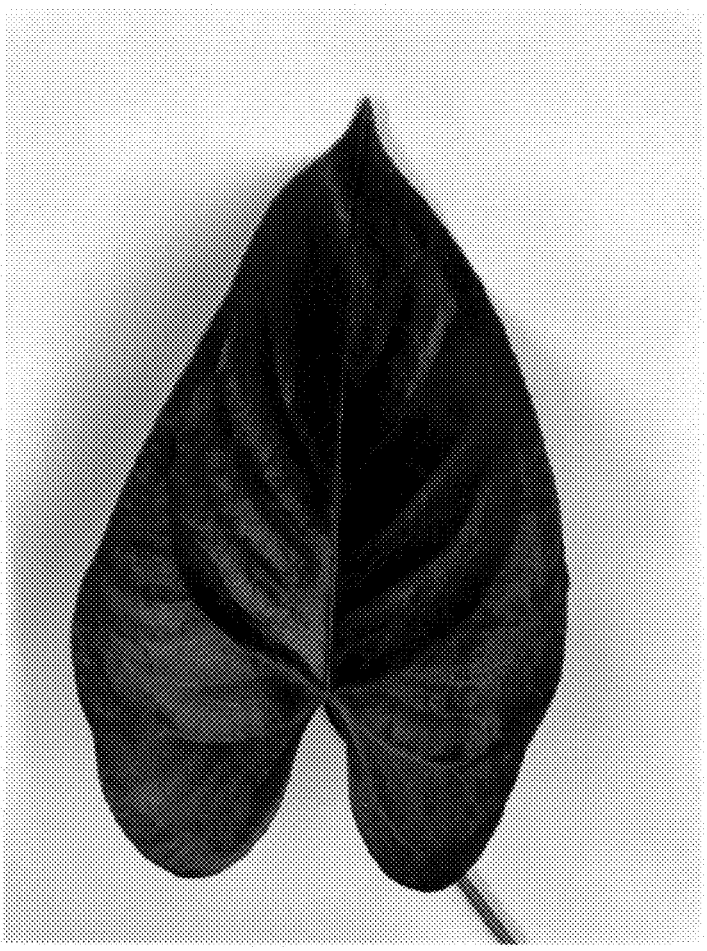
FIG. 3 shows a close-up of the upper leaf blade surface.

The following detailed description sets forth the distinctive characteristics of 'AN2429660'. The data which define these characteristics were collected from asexual reproductions carried out in Bleiswijk, the Netherlands. The plant history was taken on 44-week-old plants which were planted from tissue culture in 14-centimeter (diameter) pots and grown in a glass greenhouse between 19° C. and 24° C. Observations were made in February 2023. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'AN2429660'.

Parentage:

*Female parent*.—*Anthurium* plant '18374-04' (unpatented).

*Male parent*.—*Anthurium* plant '21958-07' (unpatented).

Plant:

*Propagation*.—Tissue culture.

*Root description*.—Fleshy-light-yellow (RHS 160D) colored roots and small, hairy lateral roots having yellow (RHS 9A) colored root tips.

*Time to produce a finished flowering plant*.—42 to 46 weeks after planting in a 14-cm (diameter) pot.

*Growth habit*.—Upright.

*Height* (*measured from soil, including inflorescence*).—38.0 cm to 43.0 cm.

*Width* (*measured from leaf tips*).—34.0 cm to 37.0 cm.

Leaves:

*Immature leaves*.—Length: 14.0 cm to 16.0 cm. Width: 9.0 cm to 10.0 cm. Color: Upper surface: RHS 146A. Lower surface: RHS 146B. Texture (both upper and lower surfaces): Glossy, leathery, and thin.

*Mature leaves*.—Length (fully expanded): 17.0 cm to 19.0 cm. Width: 10.0 cm to 12.0 cm. Shape: Ovate-cordate. Apex: Abruptly acuminate. Base: Cordate. Leaf blade angle with the petiole: Between 100 degrees and 110 degrees. Leaf margin: Entire. Color: Upper surface: RHS 147A. Lower surface: RHS 147B. Texture (upper surface): Strongly glossy, leathery, and thick. Texture (lower surfaces): Glossy, leathery, and thick. Venation: Pinnate veining; the mid-vein and primary veins (the veins that radiate out from the junction of petiole and leaf) protrude at the underside of the leaf blade. Venation color: Upper surface: RHS 146A. Lower surface: RHS 144A.

*Lobes*.—Present. Arrangement: Leaf blade has two lobes extending past the petiole. The lobes are non-touching. Length of lobes of mature leaf blades: 3.0 cm to 3.5 cm. Width of lobes of mature leaf blades: 4.0 cm to 5.0 cm. Distance from petiole/leaf junction to highest point on lobes of mature leaf blades: 2.0 cm to 4.0 cm.

*Petiole*.—Cross-section: Round. Diameter: 0.3 cm to 0.4 cm. Length: 22.0 cm to 26.0 cm for a mature leaf size. Color: Mature leaf: RHS 144A. Immature leaf: RHS 144B. Cataphyll color surrounding the petiole: Outside: RHS 144A. Inside: RHS 145B.

*Geniculum*.—Length: 2.0 cm to 2.5 cm. Width: 0.3 cm to 0.4 cm. Color: RHS 146A.

Inflorescence:

*Arrangement*.—Single.

*Flowering habit* (*length of flowering season*).—Continuous.

*Number of inflorescences per plant*.—6 to 7.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully opened, the peduncle elongates some extra centimeters.

*Arrangement*.—Spathe angle with the peduncle is between 100 degrees and 120 degrees; the spathe stands on a wiry peduncle about 4.0 cm to 7.0 cm above the foliage.

*Shape*.—Cordate.

*Apex*.—Mucronate.

*Base*.—Cordate.

*Texture*.—Weakly blistered and medium glossy.

*Margin*.—Weakly undulated.

*Size*.—Length: 7.5 cm to 8.5 cm. Width: 7.5 cm to 8.5 cm.

*Lobes*.—Present. Arrangement: The spathe has two lobes extending past the peduncle. The lobes are non-touching. Length: 1.0 cm to 1.5 cm. Width: 3.0 cm to 3.5 cm. Color: Just fully open: Upper surface: RHS 144A. Lower surface: RHS 144B. This green color remains for a very long period, at least more than weeks after opening.

Peduncle:

*Shape*.—Erect.

*Cross-section*.—Round.

*Length*.—29.0 cm to 34.0 cm.

*Diameter*.—0.2 cm to 0.3 cm.

*Color*.—RHS 144A.

Flowering time:

*General*.—One small, rooted, untreated tissue culture plant of 8.0 cm tall will flower, depending on the season, after 42 to 44 weeks and 5 to 6 blossoms appear. More blossoms appear after some additional weeks so that a full flowering and commercial plant will have 6 to 7 green spathes. Smaller blossoms may occur on immature plants.

Spadix:

*Size*.—Length: 3.0 cm to 4.0 cm (depending on flower size). Width (at apex): 0.5 cm to 0.6 cm. Width (at base): 0.5 cm to 0.6 cm.

*Shape*.—Columnar.

*Angle of spadix tip with peduncle*.—170 degrees to 180 degrees.

*Texture*.—When the spathe is unfurling, the spadix is smooth. When the spadix matures, small stigmata protrude. The stigmata are evenly distributed around the spadix. The spadix matures from base to top, slowly giving the spadix a somewhat rough appearance.

*Color*.—Immature: RHS N144C. Mature: RHS 158D. Ages to: RHS 144B.

Flowers:

*Quantity per spadix*.—100 to 130.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 160D.

Reproductive organs:

*Stamens*.—Not visible.

*Pollen amount*.—Absent.

*Pistil*.—Quantity: 100 to 130. Length: Less than 0.01 cm. Color: RHS 160D.

*Style*.—Not observed to date.

*Stigma*.—Shape: Ovoid. Diameter: Less than 0.01 cm. Color: RHS 160D.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'AN2429660' differs from the female parent plant '18374-04' (unpatented) in that 'AN2429660' has cordate, green spathes; and medium spadices, whereas '18374-04' has orbicular-cordate, light yellow-green spathes, and short spadices.

'AN2429660' differs from the male parent plant '21958-07' (unpatented) in that 'AN2429660' has medium spadices and weak blistering of the spathes, whereas '21958-07' has long spadices and medium blistering of the spathes.

'AN2429660' differs from the similar commercial variety 'ANTHLEPAM' (unpatented) in that 'AN2429660' has medium glossy, green, cordate spathes, and green spadices shortly before dehiscence of anthers, whereas 'ANTHLEPAM' has small, yellow-green, orbicular-cordate spathes, and yellow spadices shortly before dehiscence of anthers.

'AN2429660' differs from the similar commercial variety 'ANTHCUEKO' (unpatented) in that 'AN2429660' has green spathes, positioned slightly above the leaves, and medium spadices, whereas 'ANTHCUEKO' has light green spathes, positioned far above the leaves, and short spadices.

I claim:

1. A new and distinct variety of *Anthurium* plant named 'AN2429660', substantially as illustrated and described herein.

* * * * *